(12) United States Patent
Van Der Mooren et al.

(10) Patent No.: US 9,931,200 B2
(45) Date of Patent: Apr. 3, 2018

(54) OPHTHALMIC DEVICES, SYSTEMS, AND METHODS FOR OPTIMIZING PERIPHERAL VISION

(75) Inventors: Marrie Van Der Mooren, Engelbert (NL); Carmen Canovas Vidal, Groningen (NL); Henk A. Weeber, Groningen (NL); Luuk Franssen, Groningen (NL); Kaccie Y. Li, Groningen (NL); Patricia Ann Piers, Groningen (NL)

(73) Assignee: AMO GRONINGEN B.V., Groningen (NL)

( * ) Notice: Subject to any disclaimer, the term of this patent is extended or adjusted under 35 U.S.C. 154(b) by 0 days.

(21) Appl. No.: 13/594,416

(22) Filed: Aug. 24, 2012

(65) Prior Publication Data

US 2013/0226294 A1    Aug. 29, 2013

Related U.S. Application Data

(63) Continuation-in-part of application No. 12/971,506, filed on Dec. 17, 2010, now Pat. No. 8,430,508, and a continuation-in-part of application No. 12/971,607, filed on Dec. 17, 2010, now Pat. No. 8,480,228, and
(Continued)

(51) Int. Cl.
*A61F 2/16* (2006.01)
*G02C 7/04* (2006.01)

(52) U.S. Cl.
CPC .......... *A61F 2/1624* (2013.01); *A61F 2/1618* (2013.01); *A61F 2/1654* (2013.01); *G02C 7/041* (2013.01); *G02C 2202/20* (2013.01)

(58) Field of Classification Search
CPC .... A61F 2/1629; A61F 2/1654; A61F 2/1656; A61F 2/16–2/1659; A61F 2240/00; A61F 2240/001; A61F 2240/002; A61B 3/1005
USPC ............ 623/6.11, 6.24, 6.26, 6.3, 6.31, 6.28, 623/6.12; 351/159.02–159.38, 159.73, 351/159.74, 159.77, 178
See application file for complete search history.

(56) References Cited

U.S. PATENT DOCUMENTS

| | | |
|---|---|---|
| 3,367,734 A | 2/1968 | Bystricky et al. |
| 4,581,031 A | 4/1986 | Koziol et al. |
| 4,624,538 A | 11/1986 | MacFarlane |

(Continued)

FOREIGN PATENT DOCUMENTS

| | | |
|---|---|---|
| EP | 0343067 A1 | 11/1989 |
| EP | 457553 A2 | 11/1991 |

(Continued)

OTHER PUBLICATIONS

International Search Report and Written Opinion for Application No. PCT/US2012/052311, mailed on Dec. 21, 2012, 14 pages.

(Continued)

*Primary Examiner* — Darryl J Collins
*Assistant Examiner* — Gary O'Neill
(74) *Attorney, Agent, or Firm* — Johnson & Johnson Surgical Vision, Inc.

(57) ABSTRACT

The present invention relates to devices, systems, and methods for optimizing peripheral vision. In particular, methods are disclosed which include utilizing particular characteristics of the retina in optimizing peripheral vision. Additionally, various IOL designs, as well as IOL implantation locations, are disclosed which optimize peripheral vision.

15 Claims, 9 Drawing Sheets

Related U.S. Application Data a continuation-in-part of application No. 12/971,889, filed on Dec. 17, 2010, now Pat. No. 8,444,267.

(60) Provisional application No. 61/526,806, filed on Aug. 24, 2011.

(56) References Cited

U.S. PATENT DOCUMENTS

| | | | |
|---|---|---|---|
| 4,637,697 | A | 1/1987 | Freeman |
| 4,642,112 | A | 2/1987 | Freeman |
| 4,648,878 | A | 3/1987 | Kelman |
| 4,655,565 | A | 4/1987 | Freeman |
| 4,666,446 | A | 5/1987 | Koziol et al. |
| 4,778,462 | A | 10/1988 | Grendahl |
| 4,795,462 | A | 1/1989 | Grendahl |
| 4,798,608 | A | 1/1989 | Grendahl |
| 4,798,609 | A | 1/1989 | Grendahl |
| 4,828,558 | A | 5/1989 | Kelman |
| 4,932,970 | A | 6/1990 | Portney |
| 4,995,714 | A | 2/1991 | Cohen |
| 4,995,715 | A | 2/1991 | Cohen |
| 5,016,977 | A | 5/1991 | Baude et al. |
| 5,056,908 | A | 10/1991 | Cohen |
| 5,066,301 | A | 11/1991 | Wiley |
| 5,089,023 | A | 2/1992 | Swanson |
| 5,096,285 | A | 3/1992 | Silberman |
| 5,114,220 | A | 5/1992 | Baude et al. |
| 5,117,306 | A | 5/1992 | Cohen |
| 5,120,120 | A | 6/1992 | Cohen |
| 5,121,979 | A | 6/1992 | Cohen |
| 5,121,980 | A | 6/1992 | Cohen |
| 5,144,483 | A | 9/1992 | Cohen |
| 5,225,858 | A | 7/1993 | Portney |
| 5,229,797 | A | 7/1993 | Futhey et al. |
| 5,354,334 | A | 10/1994 | Fedorov et al. |
| 5,549,669 | A | 8/1996 | Jansen |
| 5,652,638 | A | 7/1997 | Roffman et al. |
| 5,683,457 | A | 11/1997 | Gupta et al. |
| 5,699,142 | A | 12/1997 | Lee et al. |
| 5,728,156 | A * | 3/1998 | Gupta ................ A61F 2/1648 351/159.17 |
| 5,748,282 | A | 5/1998 | Freeman |
| 5,760,871 | A | 6/1998 | Kosoburd et al. |
| 5,777,719 | A | 7/1998 | Williams et al. |
| 5,796,462 | A | 8/1998 | Roffman et al. |
| 5,968,094 | A | 10/1999 | Werblin et al. |
| 6,126,283 | A | 10/2000 | Wen et al. |
| 6,126,286 | A | 10/2000 | Portney |
| 6,142,625 | A | 11/2000 | Sawano et al. |
| 6,183,084 | B1 | 2/2001 | Chipman et al. |
| 6,197,057 | B1 | 3/2001 | Peyman et al. |
| 6,210,005 | B1 | 4/2001 | Portney |
| 6,338,559 | B1 | 1/2002 | Williams et al. |
| 6,457,826 | B1 | 10/2002 | Lett |
| 6,464,355 | B1 | 10/2002 | Gil |
| 6,474,814 | B1 | 11/2002 | Griffin |
| 6,488,708 | B2 | 12/2002 | Sarfarazi |
| 6,491,721 | B2 | 12/2002 | Freeman et al. |
| 6,527,389 | B2 | 3/2003 | Portney |
| 6,533,416 | B1 | 3/2003 | Fermigier et al. |
| 6,533,814 | B1 | 3/2003 | Jansen |
| 6,536,899 | B1 | 3/2003 | Fiala |
| 6,537,317 | B1 | 3/2003 | Steinert et al. |
| 6,547,822 | B1 | 4/2003 | Lang |
| 6,554,859 | B1 | 4/2003 | Lang et al. |
| 6,557,992 | B1 | 5/2003 | Dwyer et al. |
| 6,609,793 | B2 | 8/2003 | Norrby et al. |
| 6,705,729 | B2 | 3/2004 | Piers et al. |
| 6,808,262 | B2 | 10/2004 | Chapoy et al. |
| 6,830,332 | B2 | 12/2004 | Piers et al. |
| 6,846,326 | B2 | 1/2005 | Zadno-Azizi et al. |
| 6,851,803 | B2 | 2/2005 | Wooley et al. |
| 6,913,620 | B2 | 7/2005 | Lipshitz |
| 6,923,539 | B2 | 8/2005 | Simpson et al. |
| 6,923,540 | B2 | 8/2005 | Ye et al. |
| 6,986,578 | B2 | 1/2006 | Jones |
| 7,025,456 | B2 | 4/2006 | Morris et al. |
| 7,025,460 | B2 | 4/2006 | Smith, III |
| 7,036,931 | B2 | 5/2006 | Lindacher et al. |
| 7,048,760 | B2 | 5/2006 | Cumming |
| 7,061,693 | B2 | 6/2006 | Zalevsky |
| 7,073,906 | B1 | 7/2006 | Portney |
| 7,137,702 | B2 | 11/2006 | Piers et al. |
| 7,156,516 | B2 | 1/2007 | Morris et al. |
| 7,186,266 | B2 | 3/2007 | Peyman |
| 7,188,949 | B2 | 3/2007 | Bandhauer et al. |
| 7,238,201 | B2 | 7/2007 | Portney et al. |
| 7,287,852 | B2 | 10/2007 | Fiala |
| 7,293,873 | B2 | 11/2007 | Dai et al. |
| 7,365,917 | B2 | 4/2008 | Zalevsky |
| 7,377,640 | B2 | 5/2008 | Piers et al. |
| 7,410,500 | B2 | 8/2008 | Claoue |
| 7,441,894 | B2 | 10/2008 | Zhang et al. |
| 7,475,986 | B2 | 1/2009 | Dai et al. |
| 7,503,655 | B2 | 3/2009 | Smith, III |
| 7,615,073 | B2 | 11/2009 | Deacon et al. |
| 7,665,842 | B2 | 2/2010 | Ho et al. |
| 7,766,482 | B2 | 8/2010 | Smith, III et al. |
| 7,871,162 | B2 | 1/2011 | Weeber |
| 7,997,727 | B2 | 8/2011 | Ho et al. |
| 8,057,034 | B2 | 11/2011 | Ho et al. |
| 8,062,361 | B2 | 11/2011 | Nguyen et al. |
| 8,201,943 | B2 | 6/2012 | Hammer et al. |
| 8,206,442 | B2 | 6/2012 | Sel et al. |
| 8,262,728 | B2 | 9/2012 | Zhang et al. |
| 8,382,832 | B2 | 2/2013 | Deacon et al. |
| 8,430,508 | B2 | 4/2013 | Weeber |
| 8,540,365 | B2 | 9/2013 | Varnas |
| 8,862,447 | B2 | 10/2014 | Weeber |
| 9,345,570 | B2 | 5/2016 | Sieber et al. |
| 2002/0044255 | A1 | 4/2002 | Ye |
| 2002/0101564 | A1 * | 8/2002 | Herrick ................ A61F 2/1613 351/159.17 |
| 2002/0105617 | A1 | 8/2002 | Norrby et al. |
| 2002/0118337 | A1 | 8/2002 | Perrott et al. |
| 2002/0176049 | A1 | 11/2002 | Sakai et al. |
| 2003/0076478 | A1 | 4/2003 | Cox |
| 2003/0171808 | A1 | 9/2003 | Phillips |
| 2004/0021824 | A1 | 2/2004 | Ye et al. |
| 2004/0085515 | A1 | 5/2004 | Roffman et al. |
| 2004/0106992 | A1 | 6/2004 | Lang et al. |
| 2004/0111153 | A1 | 6/2004 | Woods et al. |
| 2004/0150789 | A1 | 8/2004 | Jones |
| 2004/0156014 | A1 | 8/2004 | Piers et al. |
| 2004/0230299 | A1 | 11/2004 | Simpson et al. |
| 2005/0096226 | A1 | 5/2005 | Stock et al. |
| 2005/0128432 | A1 | 6/2005 | Altmann |
| 2005/0203619 | A1 | 9/2005 | Altmann |
| 2005/0267575 | A1 | 12/2005 | Nguyen et al. |
| 2006/0009816 | A1 | 1/2006 | Fang et al. |
| 2006/0030938 | A1 | 2/2006 | Altmann |
| 2006/0034003 | A1 | 2/2006 | Zalevsky |
| 2006/0055883 | A1 | 3/2006 | Morris et al. |
| 2006/0058874 | A1 | 3/2006 | Peli |
| 2006/0066808 | A1 | 3/2006 | Blum et al. |
| 2006/0098162 | A1 | 5/2006 | Bandhauer et al. |
| 2006/0098163 | A1 | 5/2006 | Bandhauer et al. |
| 2006/0109421 | A1 | 5/2006 | Ye et al. |
| 2006/0116763 | A1 | 6/2006 | Simpson |
| 2006/0116764 | A1 | 6/2006 | Simpson |
| 2006/0116765 | A1 | 6/2006 | Blake et al. |
| 2006/0158611 | A1 | 7/2006 | Piers et al. |
| 2006/0176572 | A1 | 8/2006 | Fiala |
| 2006/0238702 | A1 | 10/2006 | Glick et al. |
| 2006/0244904 | A1 | 11/2006 | Hong et al. |
| 2006/0247766 | A1 | 11/2006 | Marin |
| 2007/0052920 | A1 | 3/2007 | Stewart et al. |
| 2007/0093891 | A1 | 4/2007 | Tabernero et al. |
| 2007/0129803 | A1 | 6/2007 | Cumming et al. |
| 2007/0171362 | A1 | 7/2007 | Simpson et al. |
| 2007/0182924 | A1 | 8/2007 | Hong et al. |
| 2007/0198083 | A1 | 8/2007 | Sel et al. |
| 2007/0268453 | A1 | 11/2007 | Hong et al. |

(56) References Cited

U.S. PATENT DOCUMENTS

| | | |
|---|---|---|
| 2008/0030677 A1 | 2/2008 | Simpson |
| 2008/0161913 A1 | 7/2008 | Brady et al. |
| 2008/0161914 A1 | 7/2008 | Brady et al. |
| 2008/0269883 A1 | 10/2008 | Das et al. |
| 2008/0269885 A1 | 10/2008 | Simpson et al. |
| 2008/0269886 A1 | 10/2008 | Simpson et al. |
| 2008/0269890 A1 | 10/2008 | Simpson et al. |
| 2008/0312738 A1 | 12/2008 | Wanders |
| 2009/0018652 A1* | 1/2009 | Hermans ............ A61F 2/1613 623/6.38 |
| 2009/0062911 A1 | 3/2009 | Bogaert |
| 2009/0164008 A1 | 6/2009 | Hong et al. |
| 2009/0187242 A1 | 7/2009 | Weeber et al. |
| 2009/0198326 A1 | 8/2009 | Zhou et al. |
| 2009/0204211 A1 | 8/2009 | Angelopoulos et al. |
| 2009/0210054 A1 | 8/2009 | Weeber et al. |
| 2009/0234448 A1* | 9/2009 | Weeber et al. ............. 623/6.3 |
| 2009/0268155 A1 | 10/2009 | Weeber |
| 2009/0268158 A1 | 10/2009 | Weeber |
| 2009/0292354 A1* | 11/2009 | Gontijo et al. ............ 623/6.11 |
| 2009/0295295 A1 | 12/2009 | Shannon et al. |
| 2009/0323020 A1 | 12/2009 | Zhao et al. |
| 2010/0016961 A1 | 1/2010 | Hong et al. |
| 2010/0100177 A1* | 4/2010 | Zhao ........................ 623/6.24 |
| 2010/0100178 A1 | 4/2010 | Weeber et al. |
| 2010/0157240 A1 | 6/2010 | Schmid et al. |
| 2010/0161048 A1 | 6/2010 | Schaper, Jr. |
| 2010/0188636 A1* | 7/2010 | Pinto et al. ................ 351/161 |
| 2011/0130833 A1 | 6/2011 | Scott et al. |
| 2011/0149236 A1 | 6/2011 | Weeber |
| 2011/0153014 A1 | 6/2011 | Zhang et al. |
| 2011/0279912 A1 | 11/2011 | Fiala |
| 2012/0277857 A1 | 11/2012 | Purchase et al. |
| 2013/0013060 A1 | 1/2013 | Zadno-Azizi et al. |
| 2013/0211515 A1 | 8/2013 | Blum et al. |
| 2014/0022649 A1 | 1/2014 | Eckhardt |
| 2014/0253877 A1 | 9/2014 | Li et al. |
| 2015/0005877 A1 | 1/2015 | Wanders |
| 2015/0250583 A1 | 9/2015 | Rosen et al. |
| 2015/0250585 A1 | 9/2015 | Rosen et al. |
| 2015/0265399 A1 | 9/2015 | Rosen et al. |
| 2015/0297342 A1 | 10/2015 | Rosen et al. |
| 2015/0320547 A1 | 11/2015 | Rosen et al. |
| 2016/0067037 A1 | 3/2016 | Rosen et al. |
| 2016/0161364 A1 | 6/2016 | Alarcon et al. |

FOREIGN PATENT DOCUMENTS

| | | |
|---|---|---|
| EP | 458508 A2 | 11/1991 |
| EP | 681198 A1 | 11/1995 |
| EP | 0926531 A1 | 6/1999 |
| EP | 949529 A2 | 10/1999 |
| EP | 1424049 A1 | 6/2004 |
| EP | 1818023 A1 | 8/2007 |
| EP | 1284687 B1 | 12/2007 |
| EP | 1310267 B1 | 1/2008 |
| EP | 1424049 B1 | 6/2009 |
| WO | WO9222264 A1 | 12/1992 |
| WO | WO9303409 A1 | 2/1993 |
| WO | WO0019906 A1 | 4/2000 |
| WO | WO0163344 A1 | 8/2001 |
| WO | WO0182839 A1 | 11/2001 |
| WO | WO0189424 A1 | 11/2001 |
| WO | WO0221194 A2 | 3/2002 |
| WO | 03000154 A2 | 1/2003 |
| WO | WO03009053 A1 | 1/2003 |
| WO | 03022137 A2 | 3/2003 |
| WO | WO2004034129 A1 | 4/2004 |
| WO | 2004049979 A1 | 6/2004 |
| WO | 2004068214 A1 | 8/2004 |
| WO | WO2004090611 A2 | 10/2004 |
| WO | WO2004096014 A2 | 11/2004 |
| WO | WO2005019906 A1 | 3/2005 |
| WO | WO2006025726 A1 | 3/2006 |
| WO | WO2006047698 A1 | 5/2006 |
| WO | WO2006060477 A2 | 6/2006 |
| WO | WO2006060480 A2 | 6/2006 |
| WO | WO2007092948 A1 | 8/2007 |
| WO | WO2007133384 A2 | 11/2007 |
| WO | WO2008045847 A2 | 4/2008 |
| WO | 2008065362 A1 | 6/2008 |
| WO | WO2009076670 A1 | 6/2009 |
| WO | 2009142961 A1 | 11/2009 |
| WO | 2012074742 A1 | 6/2012 |
| WO | 2012083143 A1 | 6/2012 |
| WO | 2013028992 A1 | 2/2013 |
| WO | 2013059041 A1 | 4/2013 |
| WO | 2013105855 A1 | 7/2013 |
| WO | 2013185855 A1 | 12/2013 |
| WO | 2015136375 A2 | 9/2015 |
| WO | 2015136380 A2 | 9/2015 |

OTHER PUBLICATIONS

Alfonso J.F., et al., "Prospective Study of the Acri.LISA bifocal Intraocular Lens," Journal of Cataract Refractive Surgery, 2007, vol. 33 (11), pp. 1930-1935.

Canovas C., et al., "Hybrid Adaptive-Optics Visual Simulator," Optical Letters, 2010, vol. 35 (2), pp. 196-198.

Cohen, Allen L., "Practical design of a bifocal hologram contact lens or intraocular lens," Applied Optics, 1992, 31 (19), 3750-3754.

Co-pending U.S. Appl. No. 12/503,267, filed Jul. 15, 2009.

Co-pending U.S. Appl. No. 12/771,550, filed Apr. 30, 2010.

Diffractive Lenses for Extended Depth of Focus and Presbyopic Correction. Presentation from Wavefront Congress held on Feb. 15, 2008, Rochester, New York.

Doskolovich L.L., et al., "Special Diffractive Lenses," SPIE, 1992, vol. 1780, pp. 393-402.

Escudero-Sanz I., et al., "Off-Axis Aberrations of a Wide-Angle Schematic Eye Model," J Opt Soc Am A Opt Image Sci Vis., 1999, vol. 16 (8), pp. 1881-1891.

Liou H.L., et al., "Anatomically Accurate, Finite Model Eye for Optical Modeling," Journal of Optical Society of America, 1997, vol. 14 (8), pp. 1684-1695.

Marsack J.D., et al., "Metrics of Optical Quality Derived From Wave Aberrations Predict Visual Performance," Journal of Vision, 2004, vol. 4 (4), pp. 322-328.

Monsoriu J.A., et al., "Devil's Lenses," Optics Express, 2007, vol. 15 (21), pp. 13858-13864.

Norrby S., et al., "Model Eyes for Evaluation of Intraocular Lenses," Applied Optics, 2007, vol. 46 (26), pp. 6595-6605.

Piers P.A., et al., "Eye Models for the Prediction of Contrast Vision in Patients with New Intraocular Lens Designs," Optics Letters, 2004, vol. 29 (7), pp. 733-735.

Piers P.A., et al., "Theoretical Comparison of Aberration-Correcting Customized and Aspheric Intraocular Lenses," Journal of Refractive Surgery, 2007, vol. 23 (4), pp. 374-384.

Siedlecki D., et al., "Radial Gradient index Intraocular Lens: a Theoretical Model," Journal of Modern Optics, 2008, vol. 55 (4-5), pp. 639-647.

Terwee T., et al., "Visualization of the Retinal Image in an Eye Model With Spherical and Aspheric, Diffractive, and Refractive Multifocal Intraocular Lenses," Journal of Refractive Surgery, 2008, vol. 24 (3), pp. 223-232.

U.S. Appl. No. 12/129,155, filed May 29, 2008.

U.S. Appl. No. 11/618,325, filed Dec. 29, 2006 (Brady et al).

U.S. Appl. No. 11/618,411, filed Dec. 29, 2006(Bradyetai).

U.S. Appl. No. 12/109,251, filed Apr. 24, 2008.

Van Meeteren A., "Calculations on the Optical Modulation Transfer Function of the Human Eye for White Light," Optica Acta, 1974, vol. 21 (5), pp. 395-412.

Vanden Berg T.J., "Analysis of Intraocular Straylight, Especially in Relation to Age," Optometry and Vision Science, 1995, vol. 72 (2), pp. 52-59.

Villegas E.A., et al., "Correlation between Optical and Psychophy, Sical Parameters as a Function of Defocus," Optometry and Vision Science, 2002, vol. 79 (1), pp. 60-67.

(56) References Cited

OTHER PUBLICATIONS

Hoffmann, et al. "Analysis of biometry and prevalence data for corneal astigmatism in 23 239 eyes", Journal of Cataract & Refractive Surgery, vol. 36, Issue 9, pp. 1479-1485.
Shammas, John H., "Intraocular Lens Power Calculations," Chapter 12, "Ultrasound Measurement of the Challenging Eye," Slack Incorporated, p. 117, Copyright 2004.
Atchison D.A., et al., "Shape of the Retinal Surface in Emmetropia and Myopia," Investigative Ophthalmology & Visual Science, 2005, vol. 46 (8), pp. 2698-2707.
Buralli D.A., et al, "Optical Performance of Holographic Kinoforms," Applied Optics, 1989, vol. 28 (5), pp. 976-983.
International Search Report and Written Opinion for Application No. PCT/IB2015/000989, mailed on Sep. 8, 2015, 13 pages.
International Search Report and Written Opinion for Application No. PCT/IB2015/001027, mailed on Sep. 8, 2015, 14 pages.
International Search Report and Written Opinion for Application No. PCT/IB2015/001244, mailed on Nov. 8, 2015, 14 pages.
International Search Report and Written Opinion for Application No. PCT/IB2015/001588, mailed on Oct. 15, 2015, 11 pages.
International Search Report and Written Opinion for Application No. PCT/IB2015/002000, mailed on Feb. 12, 2016, 12 pages.
International Search Report and Written Opinion for Application No. PCT/US2014/020343, mailed on May 15, 2014, 10 pages.
Jaeken B., et al., "Comparison of the Optical Image Quality in the Periphery of Phakic and Pseudophakic Eyes," Investigative Ophthalmology & Visual Science, 2013, vol. 54 (5), pp. 3594-3599.
Jafari-Nodoushan M., et al., "Control-Flow Checking Using Branch Instructions," IEEE/IFIP International Conference on Embedded and Ubiquitous Computing, 2008, pp. 66-72.
Oh N., et al., "Control-Flow Checking by Software Signatures," IEEE Transactions on Reliability, 2002, vol. 51 (2), pp. 111-122.
Baskaran K., et al., "Benefit of Adaptive Optics Aberration Correction at Preferred Retinal Locus," Optometry and Vision Science, 2012, vol. 89 (9), pp. 1417-1423.
Lewis P., et al., "Resolution of Static and Dynamic Stimuli in the Peripheral Visual Field," Vision Research, 2011, vol. 51 (16), pp. 1829-1834.
Lundstroma L., et al., "Symmetries in Peripheral Ocular Aberrations," Journal of Modem Optics, 2011, vol. 58 (19-20), pp. 1690-1695.
Rosen R., et al., "Adaptive Optics for Peripheral Vision," Journal of Modem Optics, 2012, vol. 59 (12), pp. 1064-1070.
Rosen R., et al., "Evaluating the Peripheral Optical Effect of Multifocal Contact Lenses," Ophthalmic and Physiological Optics, 2012, vol. 32 (6), pp. 527-534.
Rosen R., et al., "Have We Misinterpreted the Study of Hoogerheide Et Al. (1971)?," Optometry and Vision Science, 2012, vol. 89 (8), pp. 1235-1237.
Rosen R., et al., "Sign-dependent Sensitivity to Peripheral Defocus for Myopes Due to Aberrations," Investigative Ophthalmology & Visual Science, 2012, vol. 53 (11), pp. 7176-7182.
Rosen R., et al., "Influence of Optical Defocus on Peripheral Vision," Visual Psychophysics and Physiological Optics, 2011, vol. 52 (1), pp. 318-323.
Rosen R., "Peripheral Vision: Adaptive Optics and Psychophysics," Doctoral Thesis Department of Applied Physics Royal Institute of Technology Stockholm, Sweden 2013, 86 pages.
International Search Report and Written Opinion for Application No. PCT/IB2017/000553, dated Aug. 28, 2017, 19 pages.
International Search Report and Written Opinion for Application No. PCT/IB2017/000318, dated Aug. 4, 2017, 14 pages.
Liou H.L., et al., "The Prediction of Spherical Aberration with Schematic Eyes," Ophthalmic and Physiological Optics, Jan. 1996, vol. 16 (4), pp. 348-354.

\* cited by examiner

OPHTHALMIC DEVICES, SYSTEMS, AND METHODS FOR OPTIMIZING PERIPHERAL VISION

RELATED APPLICATIONS

This application claims priority to U.S. Application No. 61/526,806, filed on Aug. 24, 2011 and is continuation-in-part of the following applications: Single Microstructure Lens, Systems And Methods, U.S. patent application Ser. No. 12/971,506, filed on Dec. 17, 2010; Limited Echelette Lens, Systems And Methods, U.S. patent application Ser. No. 12/971,607, filed on Dec. 17, 2010; and Ophthalmic Lens, Systems And Methods Having At Least One Rotationally Asymmetric Diffractive Structure, U.S. patent application Ser. No. 12/971,889, filed on Dec. 17, 2010. The entire contents of the above applications are incorporated herein by reference. Full Paris Convention priority is hereby expressly reserved.

BACKGROUND OF THE INVENTION

Field of the Invention

The present invention relates generally to ocular surgical procedures involving implantable lenses, and more specifically to devices, systems and methods for optimizing peripheral vision.

Description of the Related Art

Intraocular Lenses (IOLs) may be used for restoring visual performance after a cataract or other ophthalmic procedure in which the natural crystalline lens is replaced with or supplemented by implantation of an IOL. When the optics of the eye are changed by such a procedure, the goal is to improve vision in the central field. Recent studies have found that, when a monofocal IOL is implanted, peripheral aberrations are changed, and that these aberrations differ significantly from those of normal, phakic eyes. The predominant change is seen with respect to peripheral astigmatism, which is the main peripheral aberration in the natural eye, followed by sphere, and then other higher order aberrations. Such changes may have an impact on overall functional vision, on myopia progression, and—for newborns and children—on eye development.

There are also certain retinal conditions that reduce central vision, such as AMD or a central scotoma. Other diseases may impact central vision, even at a very young age, such as Stargardt disease, Best disease, and inverse retinitis pigmentosa. For these patients, peripheral vision is of particular importance. Accordingly, better devices, systems and methods are needed for optimizing peripheral vision.

SUMMARY OF THE INVENTION

The present invention includes intraocular lenses (IOLs) including, for example, phakic IOLs and piggyback IOLs which are optimized to improve peripheral vision. For normal patients, e.g. uncomplicated cataract patients, peripheral vision may be balanced with good central vision in order to maximize overall functional vision. For those patients having a pathological loss of central vision, peripheral vision may be maximized, taking into account the visual angle where the retina is healthy.

In one embodiment, the principal plane of the lens is moved posteriorly or closer to the nodal point of the eye as compared to standard IOLs. This effectively changes the field curvature in the image plane, to better align with the shape of the retina. In a preferred embodiment, the axial position of the IOL is between about 1.5 mm and about 2.5 min behind the iris. For example, the axial position of the IOL may be about 1.9 mm behind the iris. In another preferred embodiment, the axial position of the IOL is between about 2.5 mm and about 3.5 mm behind the iris. For example, the axial position of the IOL may be about 2.9 mm behind the iris. In another preferred embodiment, the axial position of the IOL may be between about 3.5 mmn and about 4.1 mm behind the iris. For example, the axial position of the IOL may be about 3.9 mm behind the iris. For regular eye dimensions, the position of the lens may be limited by the vitreous body, to not exceed about 4.5 mm behind the iris. For the lenses used in this example, the principal plane is about 0.4 mm posterior to the anterior lens surface. Therefore, when the example refers to a distance of the lens of e.g. 1.5 mm behind the iris, the principal plane of the lens is about 1.9 mm behind the iris.

Instead of moving the lens posteriorly, a lens configuration may be applied that moves the principal plane of the lens posteriorly, while the physical lens is still in the conventional position in the eye. One way to achieve this is to change the shape factor of the lens, e.g. to a meniscus lens having a concave anterior surface and a convex posterior surface. In an alternative embodiment, an intraocular lens system of 2 lenses is used, e.g. having a negative power anterior lens and a positive power posterior lens. Those skilled in the art will appreciate that other combinations are possible.

The lens may be a multifocal lens, a lens including a prism, or a telescope lens, having the principal plane moved posteriorly by one of the methods described above. In a multifocal lens, the invention may be applied on one focal point, on several of the focal points, or on all focal points of the multifocal lens. In a preferred embodiment, a multifocal IOL has at least 2 zones, wherein the at least 2 zones have about the same optical power. The inner zone may be a spherical lens producing a good central focus. The outer zone(s) comprise of a spherical lens combined with a prism, producing a good focus at a predetermined spot in the periphery. A similar affect may be achieved if the outer zone(s) are aspheric. Alternatively, a bag-filling lens with a gradient refractive index may be used.

In another embodiment, an artificial pupil may be implanted between the lenses of a dual lens system or posterior to an IOL or lens combination. Such an artificial pupil may have a similar impact as moving the IOL posteriorly.

In another embodiment, a singular circular surface structure, which acts as a phase shifting profile, as detailed in U.S. application Ser. No. 12/971,506 extends the depth of focus in the peripheral field. An exemplary single ring IOL includes an anterior face and a posterior face. A profile can be imposed on the anterior or posterior surface or face. The profile can have an inner portion and an outer portion. The inner portion typically presents a parabolic curved shape. The inner portion may also be referred to as a microstructure, an isolated echelette, or a central echelette. Between the inner portion and the outer portion, there may be a transition zone that connects the inner and outer portions. An IOL with such a structure provides for a reduction in peripheral aberrations, including astigmatism and other higher order aberrations. In another embodiment, a multifocal IOL is used to induce multiple foci. While traditional multifocal IDLs utilize multiple foci at multiple powers, in this preferred embodiment, the multiple foci are of the same optical power. In addition, the multiple foci focus images on different parts of the retina, thus producing optimal optical quality at those regions of the retina that are healthy.

In another embodiment, characteristics of the retina are considered for the IOL design. In particular, a geographical map of retinal functionality and/or the retinal shape are combined with other ocular geometry, such as pupil size and location, axial positions of the pupil, lens, and retina, anterior and/or posterior corneal aberrations, tilts and decentrations within the eye, and angle kappa. Optimization occurs using a metric function which includes both central and peripheral optical quality.

Thus, the present invention provides a lens apparatus, system and method that improve peripheral visual acuity.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE DRAWINGS

The present invention generally provides devices, systems, and methods for optimizing peripheral vision.

The following disclosure will be primarily directed to embodiments of the invention as they apply to implantable intraocular lenses; however, it is understood that other embodiments may be applied directly, or indirectly, to other types of ophthalmic lenses including, but not limited to, corneal implants, corneal surgical procedures such as LASIK or PRK, contact lenses, and other such devices. In some embodiments, various types of ophthalmic devices are combined, for example, an intraocular lens and a LASIK procedure may be used together to provide a predetermined visual outcome. Embodiments of the invention may also find particular use with multifocal or accommodating intraocular lenses.

Figure 1:
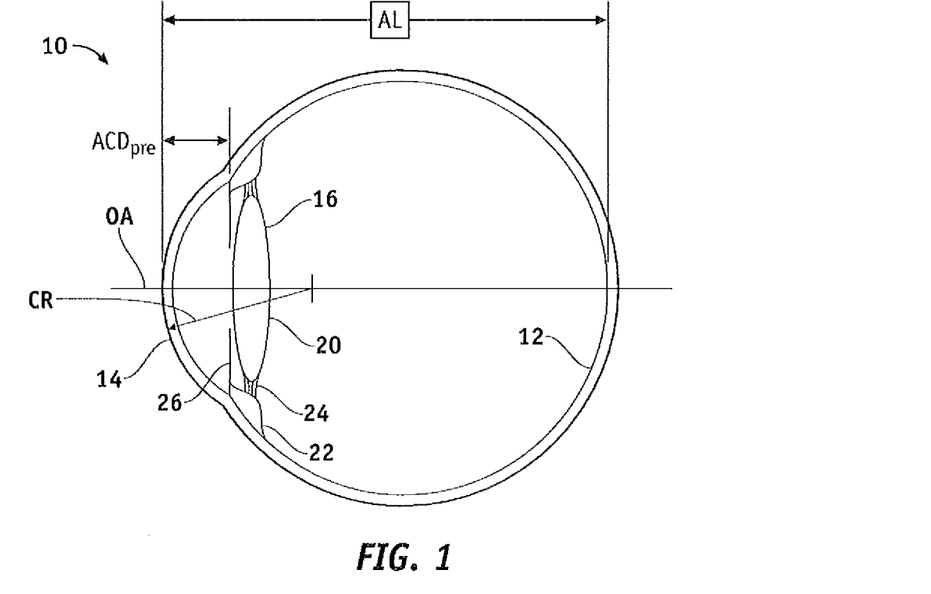
FIG. 1 is a cross-sectional view of a phakic eye containing a natural crystalline lens.

Embodiments of the invention may be understood by reference to FIG. 1, which is a cross-sectional view of a phakic eye with the natural crystalline lens, an eye 10 comprises a retina 12 that receives light in the form of an image that is produced by the combination of the optical powers of a cornea 14 and a natural crystalline lens 16, both of which are generally disposed about an optical axis OA. As used herein, an "anterior direction" is in the direction generally toward the cornea 14, while a "posterior direction" is generally in the direction toward the retina 12.

The natural lens 16 is contained within a capsular bag 20, which is a thin membrane that completely encloses the natural lens 16 and is attached to a ciliary muscle 22 via zonules 24. An iris 26, disposed between the cornea 14 and the natural lens 16, provides a variable pupil that dilates under lower lighting conditions (scotopic vision) and contracts under brighter lighting conditions (photopic vision). The ciliary muscle 22, via the zonules 24, controls the shape and position of the natural lens 16, which allows the eye 10 to focus on both distant and near objects. Distant vision is provided when the ciliary muscle 22 is relaxed, wherein the zonules 24 pull the natural lens 16 so that the capsular bag 20 is generally flatter and has a longer focal length (lower optical power). Near vision is provided as the ciliary muscle contracts, thereby relaxing the zonules 24 and allowing the natural lens 16 to return to a more rounded, unstressed state that produces a shorter focal length (higher optical power).

The optical performance of the eye 10 also depends on the location of the natural lens 16. This may be measured as the spacing between the cornea 14 and the natural lens which is sometimes referred to as the anterior chamber depth prior to an ocular surgical procedure, $ACD_{pre}$.

Figure 2:
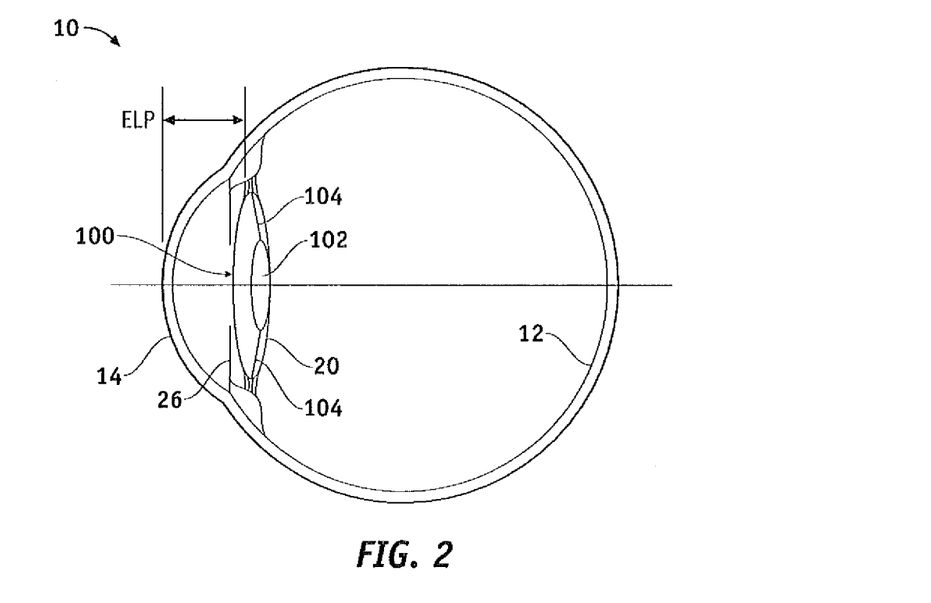
FIG. 2 is a cross-sectional view of a pseudophakic eye containing an intraocular lens.

Referring additionally to FIG. 2, which is a cross-sectional view of a pseudophakic eye 10, the natural crystalline 16 lens has been replaced by an intraocular lens 100 according to an embodiment of the present invention. The intraocular lens 100 comprises an optic 102 and haptics 104, the haptics 104 being generally configured to center the optic 102 within the capsular bag 20. Numerous configurations of haptics 104 relative to optic 102 are well know within the art and embodiments of the present invention may be applied to any of these. For purposes of the embodiments disclosed herein, the location of the intraocular lens is measured as the spacing between the iris and the anterior surface of the lens. For the lenses used in this example, the principal plane is about 0.4 mm posterior to the anterior lens surface. Therefore, when the example refers to a distance of the lens of e.g. 1.5 mm behind the iris, the principal plane of the lens is about 1.9 mm behind the iris.

Figure 3:
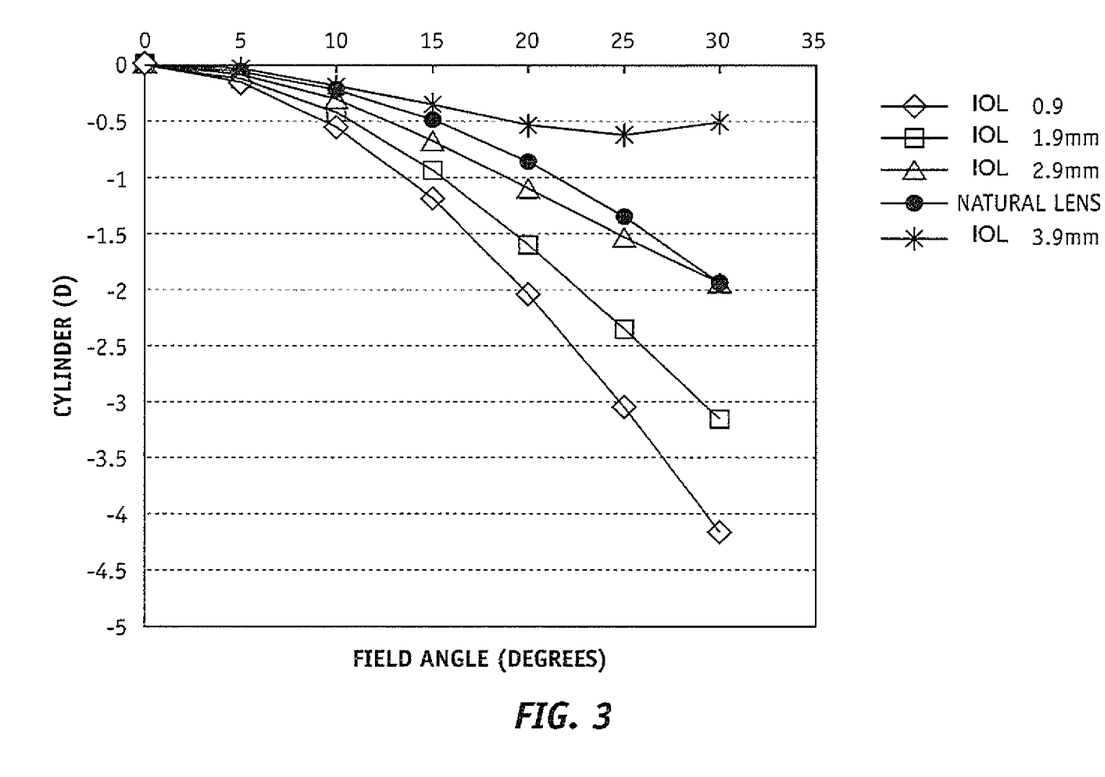
FIG. 3 is a graph illustrating peripheral astigmatism with the field angle in degrees and cylinder in diopters.
Figure 4:
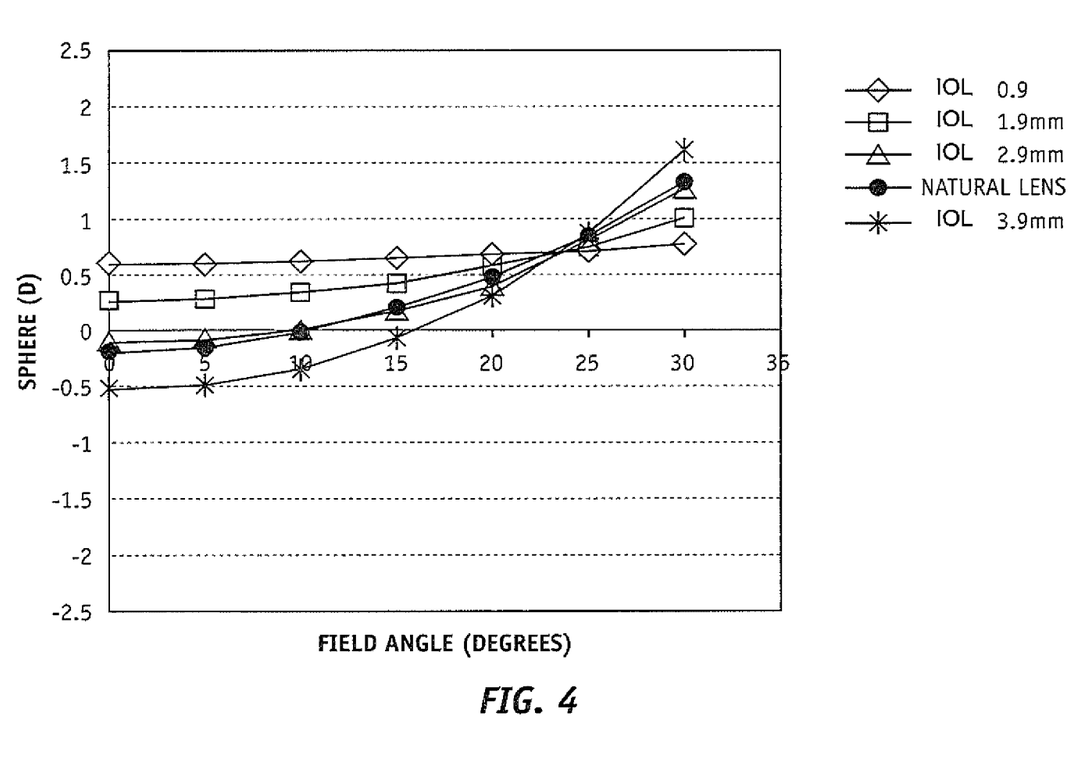
FIG. 4 is a graph illustrating peripheral astigmatism with the field angle in degrees and sphere in diopters.
Figure 5:
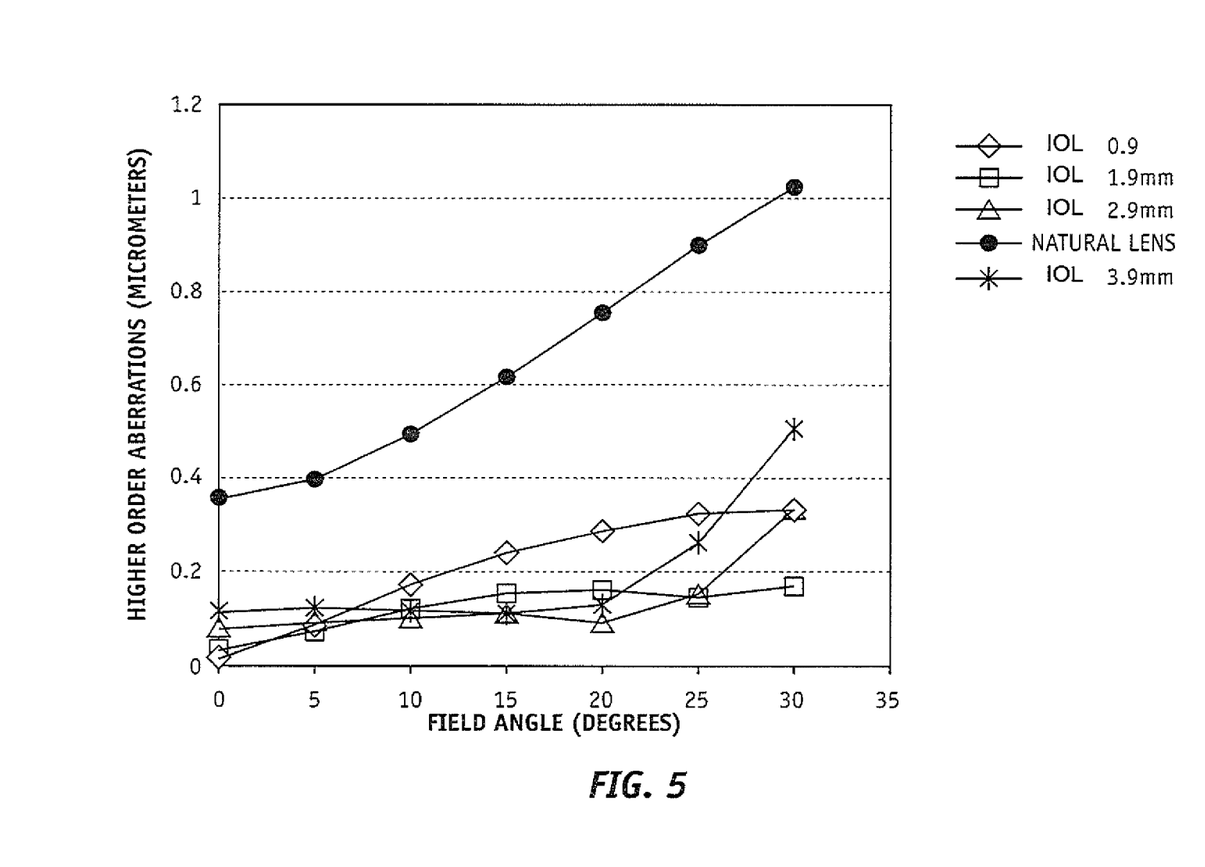
FIG. 5 is a graph illustrating peripheral astigmatism with the field angle in degrees and higher order aberrations in micrometers.

In one embodiment, the principal plane of the lens is moved posteriorly or closer to the nodal point of the eye as compared to standard IOLs. As seen in FIGS. 3-5, placing the IOL posteriorly improves peripheral vision. For purposes of the calculations detailed in FIGS. 3-5 an eye model from the following publication was used: Escudero-Sanz, I., & Navarro, R. "Off-axis aberrations of a wide-angle schematic eye model" *J. Opt. Soc. Am. A. Opt. Image Sci. Vis.*, vol. 16 (8), pp. 1881-1891, 1999, the contents of which are incorporated herein by reference.

The peripheral aberrations of the natural eye were calculated according to this reference and are disclosed in FIGS. 3-5 as the "natural lens," The natural lens was replaced by a standard monofocal IOL. The axial position of the principal plane of the lens is typically about 0.9 mm behind the iris. The peripheral refraction (sphere and cylinder) were then calculated for different axial positions of the IOL (as measured from the iris).

The graphs show that the peripheral astigmatism is reduced considerably when the lens is placed further posteriorly in the eye (FIG. 3), while having limited impact on peripheral sphere (FIG. 4), and no impact on higher order aberrations (FIG. 5). The graphs also show that when the lens is placed about 2.9 mm behind the iris (which is about 2.0 mm posterior to the current normal position of an IOL), the peripheral refraction (sphere and astigmatism) is about the same as that of the natural eye. As current IOLs are located more or less at the equator of the capsular bag, a position of 2.0 mm more posteriorly means that the lens is positioned about against the vitreous. Since the natural lens is about 4.5 mm thick, there is space to place the IOL further posteriorly.

Various lens haptic/optic configurations may be implemented in order to place the optic further posteriorly. For example the haptics may be anteriorly angled such that when the IOL is placed in the eye, the optic portion is vaulted posteriorly. "Virtual" posterior placement of the IOL may be achieved by changing the shape factor of the IOL such that the distribution power of the lens is such that more power is on the posterior side. For a single optic, this can be done using a meniscus lens, having negative power at the anterior surface and positive power at the posterior surface. For a dual optic design, this can be achieved by having an anterior lens with a negative power, and a posterior lens with a positive power. Increasing the lens thickness is another option disclosed herein.

Yet another option is to apply an optical system making use of 3 lenses. Such lens systems are capable of optimizing field curvature, as well as astigmatism.

In another embodiment, an artificial pupil may be implanted between the lenses of a dual lens system, or posterior to an IOL or lens combination. Such an artificial pupil may have a similar impact as it changes the peripheral aberrations.

In another embodiment, peripheral vision is improved by an IOL design having an extended depth of focus in the periphery. There are several methods to extend the depth of focus that can be applied. Below is a specific example, based on extending the depth of focus with a single ring microstructure.

Figure 6:
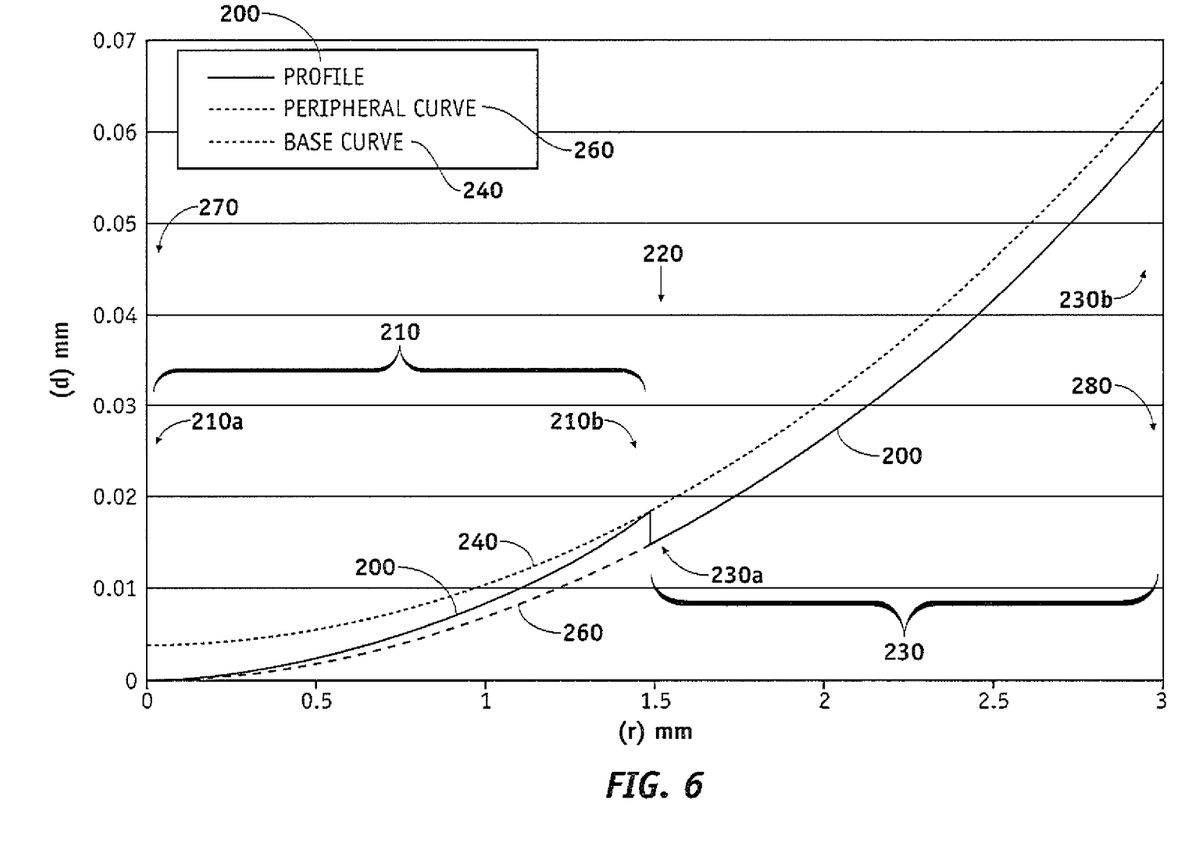
FIG. 6 shows aspects of a single microstructure lens according to embodiments of the present invention.

FIG. 6 discloses a single ring microstructure for extending depth of focus as detailed in U.S. patent application Ser. No. 12/971,506. Only half of the lens is shown in FIG. 6, although since the single ring microstructure is rotationally symmetric, the other half is a mirror image that complements the lens at the left side of FIG. 6. Profile 200 of the single ring surface includes an inner portion or single ring 210, a step or transition 220, and an outer portion 230. Inner portion 210 extends between a central location 270 of profile 200 and transition 220, and outer portion 230 extends between transition 220 and a peripheral location 280 of profile 200. Central location 270 is typically disposed at the optical axis. Transition 220 is disposed at a distance of about 1.5 mm from the optical axis, and peripheral location 280 is disposed at the diameter of the clear aperture of the lens, here at a distance of about 3.0 mm from the optical axis. In some cases, transition 220 can be disposed at a distance from the optical axis that is within a range from about 0.5 mm to about 2.0 mm, and peripheral location 280 can be disposed at a distance from the optical axis that is within a range from about 2.0 to about 3.5 mm, or bigger (for example, for contact lenses, the ranges would be scaled due to the larger sizes of the contact lens compared to an IOL).

As shown in FIG. 6, the surface height or sag (d) from a reference plane perpendicular to the optical axis, of each point on the lens profile is plotted against the radial distance (r) from the optical axis of the lens. As shown here, the value of displacement or total sag (d) can have a value within a range from about 0 mm to about 0.07 mm. The total sag can depend on the refractive shape of the surface and can have a value, for an IOL, of typically between 0 mm and about 2 mm, or to about minus 2 mm, in cases where the surface is concave.

Inner Portion

Inner portion or echelette 210 includes a center 210a and a peripheral edge 210b. At center or central section 210a of inner portion 210, the sag (d) of inner portion 210 is substantially equivalent to the displacement or sag (d) of peripheral curve 260. At peripheral edge 210b, the sag (d) of inner portion 210 is substantially equivalent to the sag (d) of diffractive base curve 240. Where radial distance (r) is zero, sag (d) of inner portion 210 is equivalent to the value of the peripheral curve 260. The value of sag (d) between radial distance zero and radial distance at the peripheral edge 210b, for example at 1.5 mm, gradually and smoothly changes from the value of peripheral curve 260 (at r=0) to diffractive base curve 240 (at 1-1.5 mm) in a parabolic fashion. As shown here, inner portion 210 can present a parabolic shape, for example as described in Equation 4a of Cohen, Applied Optics, 31:19, pp. 3750-3754 (1992), incorporated herein by reference.

Transition

At the peripheral edge 210b, where the radial distance (r) is 1.5 mm, the value of sag (d) steps or changes from the value of diffractive base curve 240 to the value of peripheral curve 260. Where radial distance (r) corresponds to transition 220, sag (d) of inner portion 210 is equivalent to the value of the diffractive base curve 240. Relatedly, the displacement of the profile 200 approaches that of the peripheral curve 260 as the radial distance increases from a value of zero to a value of about 1.5 mm. The value of the offset can be determined along the vertical axis. The offset value may be selected depending on the amount of phase delay. According to one embodiment, the inner portion 210 and the outer portion 230 may not end up at the same vertical height at position 210b/230a. One way to connect these two endpoints is by using a straight vertical line. As shown here, the diffractive transition step provides a sharp step in the profile. In some cases the transition is characterized by a step height having a value within a range from about 0.5 microns and about 4 microns.

Outer Portion

Outer portion 230 includes an inner or central edge 230a and a peripheral edge 230b. At inner edge 230a, the sag (d) of outer portion 230 is substantially equivalent to the sag (d) of peripheral curve 260. At peripheral edge 230b, the sag (d) of outer portion 230 remains substantially equivalent to the sag (d) of peripheral curve 260. The value of sag (d) for the outer portion 230 of profile 100 between radial distance 1.5 mm and radial distance 3.0 mm is equivalent to the value of peripheral curve 260. The sag of the profile 200 and the peripheral curve 260 are approximately equivalent between radial distance values of 1.5 mm and 3.0 mm.

In addition to a single ring, limited ring extended depth of focus embodiments, as disclosed in application Ser. No. 12/971,607, comprise of adding a limited number of echelettes to the above detailed single ring microstructure. In general such limited ring embodiments comprise of a limited number of echelettes that are either adjacent or non-adjacent to the inner central echelette and may or may not be separated by a refractive region. It should be appreciated that any variation of single and limited ring embodiments falls within the scope of this invention.

Figure 7:
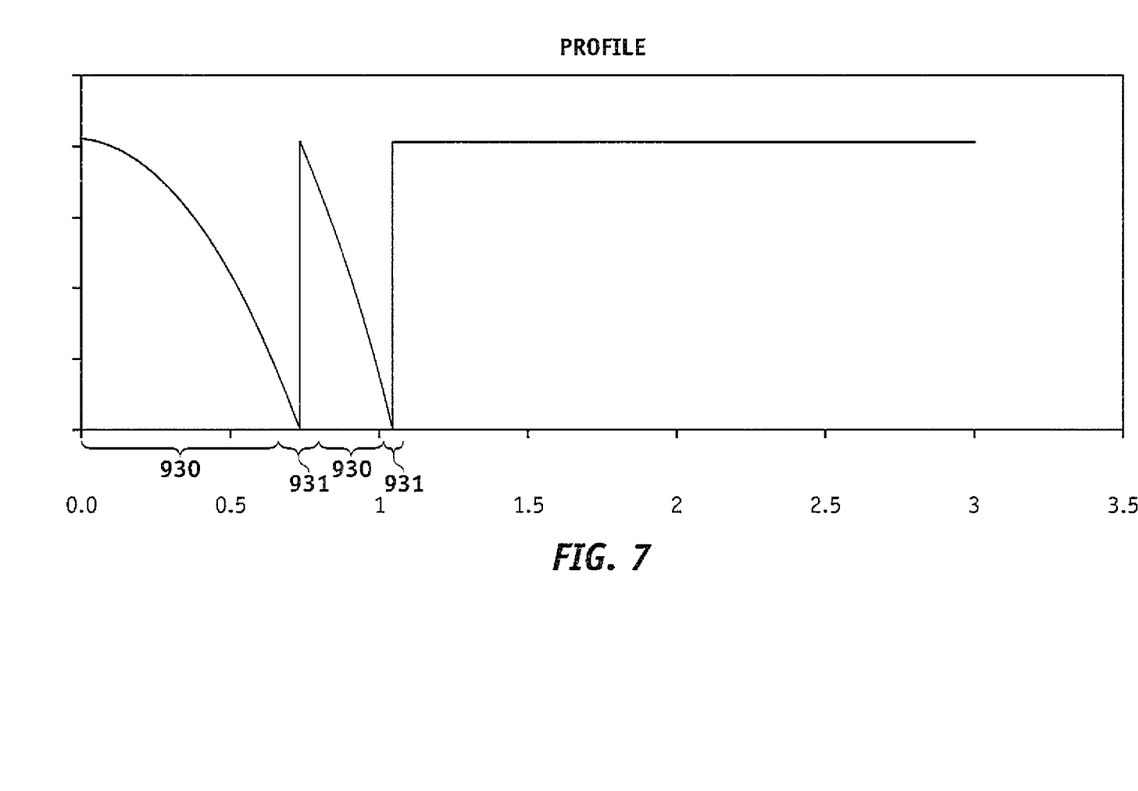
FIG. 7 illustrates aspects of a lens profile according to embodiments of the present invention.

FIG. 7 provides a graphical representation of a portion of a lens diffractive profile with a central echelette and one peripheral adjacent echelette according to embodiments of the present invention. In FIG. 7, the height of the surface relief profile (from a plane perpendicular to the light rays) of each point on the echelettes surface is plotted against the distance from the optical axis of the lens. The echelettes can have a characteristic optical zone 930 and transition zone 931. Optical zone 930 can have a shape or downward slope that may be linear when plotted against ρ as shown in FIG. 7. When plotted against radius r, optical zone 930 can have a shape or downward slope that is parabolic. Central and peripheral echelettes can have a surface area that is between 0.7 and 7 mm$^2$. For example, the echelettes may have a surface area that is 0.85 mm$^2$. An outer (refractive) zone can follow the base radius with a fixed offset. Exemplary embodiments include peripheral echelette(s) that are similar in shape (e.g. elliptical) and variable stepheight as the central echelette. Of course, this invention includes those embodiments where the peripheral echelette(s) differ in shape and/or variable stepheight as compared to the central echelette.

Figure 8:
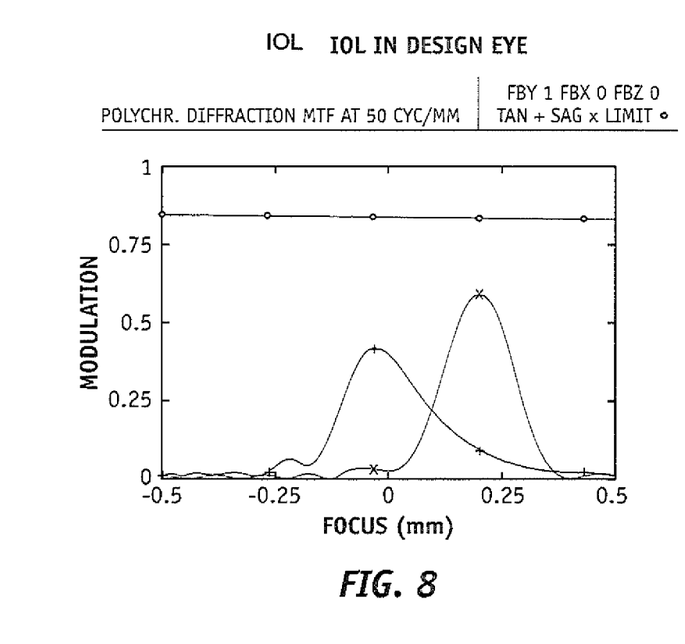
FIG. 8 is a graph illustrating through-focus MTF at different axial focus positions.
Figure 9:
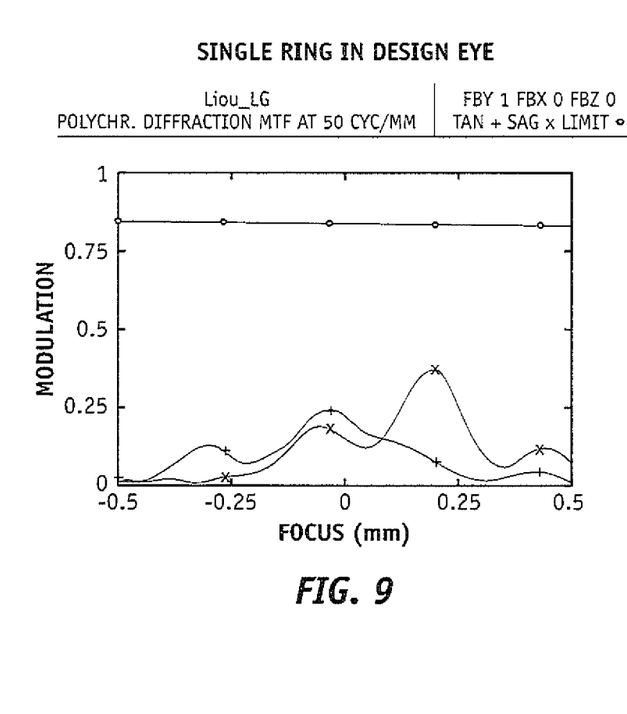
FIG. 9 is a graph illustrating through-focus MTF at different axial focus positions.

It has been determined that these aforementioned structures extend the depth of focus and reduce aberrations in the peripheral field. As seen in FIGS. 8 and 9, the extended depth of focus IOL has no significant peripheral astigmatism as compared to a standard monofocal IOL. A standard monofocal chromatic IOL was used in a schematic eye model, based on the following Liou & Brennan publication: Liou, H. L., & Brennan, N. A., "Anatomically accurate, finite model eye for optical modeling" *J Opt Soc Am A*, 14 (8), 1684-1695 1997, with a retinal radius of curvature of 12 mm, a pupil diameter of 3 mm. The through focus white light MTF at 50 c/mm was calculated at the periphery, 15 degrees off-axis in 2 perpendicular orientations (tangetial and sagital). As seen in FIG. 8, the monofocal IOL has 2 peaks at different axial focus positions for the 2 orientations. This is caused by astigmatism. As seen in FIG. 9, the single ring extended depth of focus IOL, at zero defocus, had an MTF in both orientations about equally high, indicating that there is no significant astigmatism. Thus, the monofocal IOL generates astigmatism in the periphery, while the extended depth of focus IOL does not.

While other solutions may have a very specific influence on a particular peripheral wavefront aberration, an extended depth of focus in the periphery is relatively insensitive to specific aberrations and dimensions of the eye of a particular patient. Additionally, such an extended depth of focus solution also has an increased tolerance to possible issues related to surgically induced changes of aberrations, as well as IOL placement issues. Therefore, it can be used as a one-size-fits-all solution.

Analogously, movement of the IOL posteriorly or closer to the nodal point also provides for a more general solution as opposed to an IOL which has a particular design to address particular aberrations.

In another embodiment, a multifocal IOL is used to induce multiple foci of the same optical power. In other words, unlike traditional multifocal IOLs, the add power for the present invention is about zero. In addition, the multiple foci focus images on different parts of the retina, thus producing optimal optical quality at those regions of the retina that are healthy, or alternatively in a ratio that optimizes vision.

Figure 10:
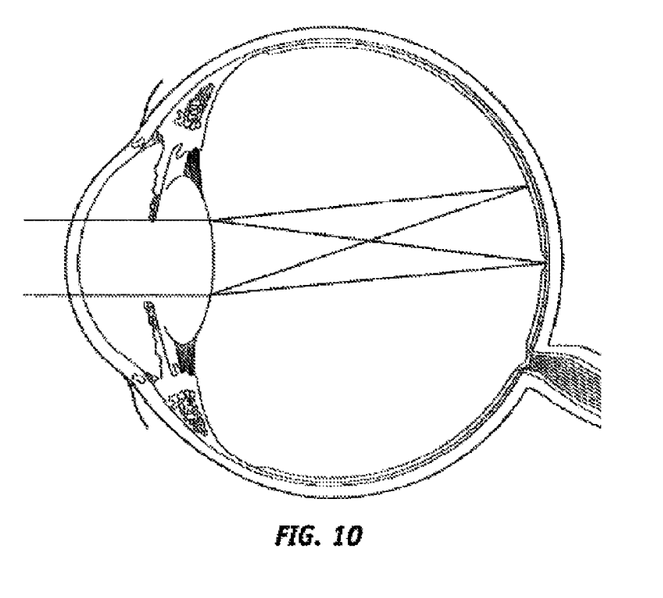
FIG. 10 shows aspects of a multifocal IOL in an eye.
Figure 10A:
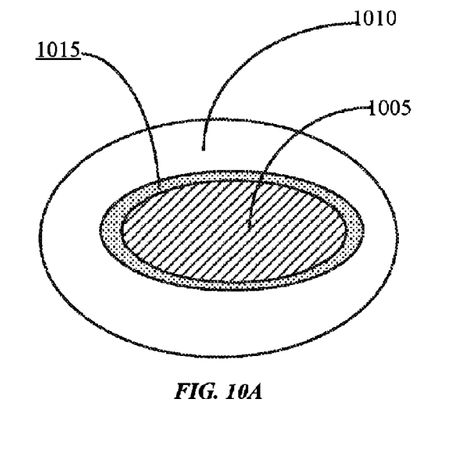
FIG. 10A illustrates an embodiment of an intraocular lens having 2 zones connected by a transition zone.

In a preferred embodiment, a multifocal IOL has at least 2 zones, wherein the at least 2 zones have about the same optical power. FIG. 10A illustrates an embodiment of an intraocular lens having 2 zones 1005 and 1010 connected by a transition zone 1015. The inner zone 1005 may be a spherical lens producing a good central focus on the central fovea. The outer zone(s) (e.g., 1010) consist of a spherical lens combined with a prism, producing a good focus at a predetermined spot in the periphery as seen in FIG. 10. One skilled in the art will appreciate that many zone variations are possible including, but not limited to concentric or non-concentric variations. Additionally more than two images may be formed, and the light distribution may be varied in order to optimize visual acuity. The multifocal lens has a small add power, typically smaller than about 6 diopters. Preferably, the multifocal lens has an add power of less than about 4 diopters. In another preferred embodiment, the multifocal lens has an add power of less than about 2 diopters. Preferably the add power is about equal to zero.

Similar effects may be achieved through the use of outer zone(s) which are aspheric. Alternatively, diffractive optics may be used to induce multiple foci on different parts of the retina with the same optical power. The present invention also includes a bag-filling lens with a gradient refractive index to achieve the same result.

In another embodiment, characteristics of the retina are considered for the IOL design. In particular, a geographical map of retinal functionality and/or the retinal shape are combined with other ocular geometry, such as pupil size and location, axial positions of the pupil, lens, and retina, anterior and/or posterior corneal aberrations, tilts and decentrations within the eye, and angle kappa. The shape of the retina may be measured using MRI, tomography, or other techniques apparent to those skilled in the art. Optimization occurs using a metric function which includes both central and peripheral optical quality. Optical quality is measured taking into account any particular damage to the fovea or other region of the retina. For example, the size and location of a possible retinal scotoma may be determined. If the patient has a central scotoma which covers the entire fovea, then maximizing visual acuity in the peripheral region would be incorporated into the optical design.

Such maximization of peripheral vision would be dependent on the peripheral threshold MTF, which depends on cone/rod size and spacing. For example, the large con/rod spacing seen in the periphery limits the spatial resolution. Thus, the maximum optical quality in the periphery would be less than or equal to the peripheral threshold MTF, and optimizing optical quality at a higher level would not result in better visual acuity.

Additionally, recent data suggests that peripheral optics in myopes differs from that in emmetropes. Thus, customizing an IOL to account for particular peripheral aberrations while balancing peripheral MTF may lead to improved overall vision.

Figure 11:
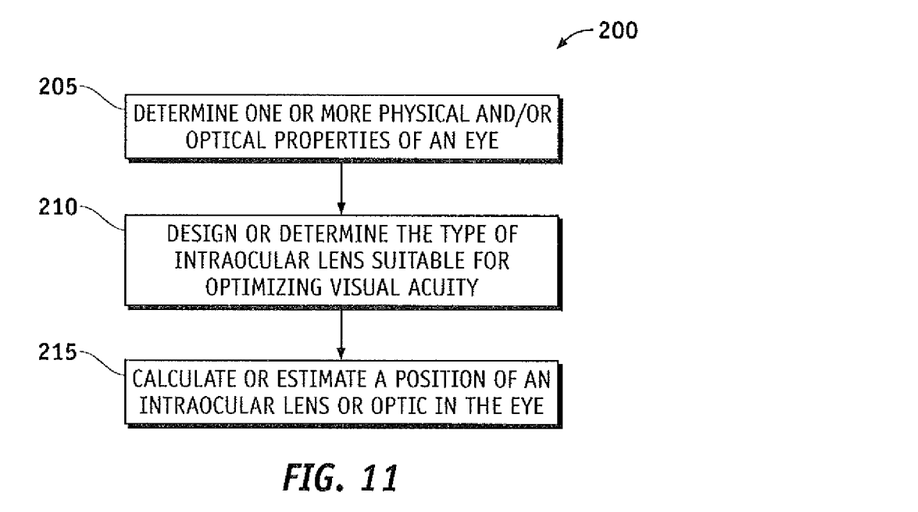
FIG. 11 is a flow chart of a method according to an embodiment of the present invention.

Referring to FIG. 11, in certain embodiments, a method 200 for optimizing peripheral vision comprises an element 205 of determining one or more physical and/or optical properties of the eye 100 including a geographical map of retinal functionality and/or the retinal shape.

The method 200 additionally comprises an element 210 of either designing or determining the type of intraocular lens 100 suitable for optimizing visual acuity, including peripheral visual acuity. The design of the lens may be of any detailed herein, as well as modifications and alternate constructions that come within the spirit and scope of the invention.

The method 200 also comprises an element 215 of calculating a desired position of the intraocular lens 100 or the optic 102 after an ocular surgical procedure.

Referring to FIG. 11, in certain embodiments, a computer system 300 for optimizing peripheral vision comprises a processor 302 and a computer readable memory 304 coupled to the processor 302. The computer readable memory 304 has stored therein an array of ordered values 308 and sequences of instructions 310 which, when executed by the processor 302, cause the processor 302 to calculate a post-operative lens position within an eye and/or for selecting an ophthalmic lens or an optical power thereof. The array of ordered values 308 may comprise, for example, one or more ocular dimensions of an eye or plurality of eyes from a database, a desired refractive outcome, parameters of an eye model based on one or more characteristics of at least one eye, and data related to an IOL or set of IOLs such as a power, an aspheric profile, and/or a lens plane. In some embodiments, the sequence of instructions 310 includes determining a position of an IOL, performing one or more calculations to determine a predicted refractive outcome based on an eye model and a ray tracing algorithm, comparing a predicted refractive outcome to a desired refractive outcome, and based on the comparison, repeating the calculation with an IOL having at least one of a different power, different design, and/or a different IOL location.

Figure 12:
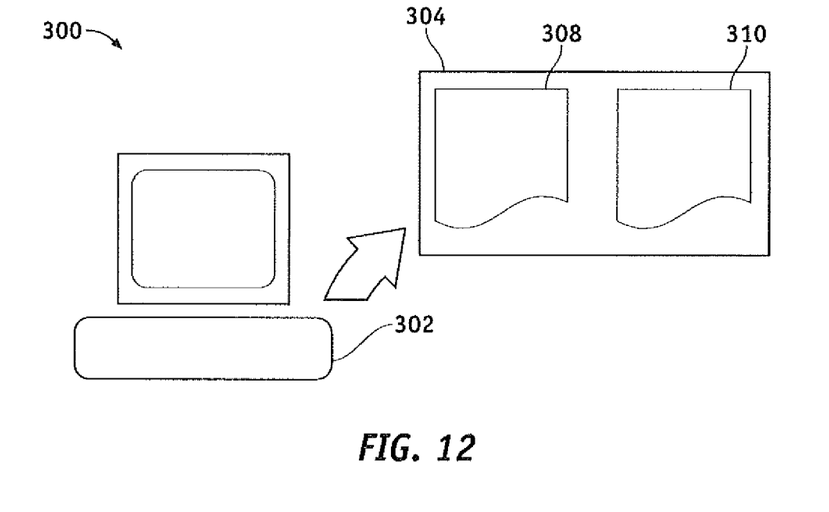
FIG. 12 is a graphical representation of the elements of computing system for selecting an ophthalmic lens according to an embodiment of the present invention.

The computer system 300 may be a general purpose desktop or laptop computer or may comprise hardware specifically configured performing the desired calculations. In some embodiments, the computer system 300 is configured to be electronically coupled to another device such as a phacoemulsification console or one or more instruments for obtaining measurements of an eye or a plurality of eyes. In other embodiments, the computer system 300 is a handheld device that may be adapted to be electronically coupled to one of the devices just listed. In yet other embodiments, the computer system 300 is, or is part of, refractive planner configured to provide one or more suitable intraocular lenses for implantation based on physical, structural, and/or geometric characteristics of an eye, and based on other characteristics of a patient or patient history, such as the age of a patient, medical history, history of ocular procedures, life preferences, and the like.

Generally, the instructions of the system 300 will include elements of the method 300 and/or parameters and routines for performing calculations of one or more of Equations above.

In certain embodiments, the system 300 includes or is part a phacoemulsification system, laser treatment system, optical diagnostic instrument (e.g, autorefractor, aberrometer, and/or corneal topographer, or the like). For example, the computer readable memory 304 may additionally contain instructions for controlling the handpiece of a phacoemulsification system or similar surgical system. Additionally or alternatively, the computer readable memory 304 may additionally contain instructions for controlling or exchanging data with an autorefractor, aberrometer, tomographer, and/or topographer, or the like.

In some embodiments, the system 300 includes or is part of a refractive planner. The refractive planner may be a system for determining one or more treatment options for a subject based on such parameters as patient age, family history, vision preferences (e.g., near, intermediate, distant vision), activity type/level, past surgical procedures.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A method of optimizing peripheral vision, comprising:
determining one or more physical and/or optical properties of a retina;
selecting an IOL based on the one or more physical properties of the retina, wherein the IOL is rotationally symmetric about an axis intersecting the retina at the fovea when implanted in an eye of a patient, the IOL having an anterior surface and a posterior surface, the IOL being configured to receive ambient light refracted from the cornea of the eye, the IOL configured to focus at least a portion of on-axis incident light at a spot in a peripheral location of the retina that is spaced away from the foveal region of the retina; and
selecting an axial position of the IOL such that the anterior surface of the IOL is positioned at a distance greater than about 2.5 mm and less than about 3.5 mm behind the iris of the eye having regular dimensions, the selected axial position of the IOL configured to optimize optical quality at the spot in the peripheral location of the retina to be less than or equal to a peripheral threshold MTF at the spot in the peripheral location of the retina, the peripheral threshold MTF being dependent on one or more physical and/or optical properties of the retina.

2. The method of claim 1, wherein the optical properties of the retina include a geographical map of retinal functionality.

3. The method of claim 1, wherein the optical properties of the retina include the shape of the retina.

4. The method of claim 1, wherein determining one or more physical and/or optical properties of a retina includes measuring a shape of the retina of a patient or determining a size and location of a retinal scotoma in a patient.

5. The method of claim 1, further comprising implanting the selected IOL in the eye of the patient.

6. The method of claim 1, further comprising selecting an axial position of the IOL such that a distance between the anterior surface of the IOL and the iris of the eye having regular dimensions is at least 2.9 mm.

7. The method of claim 1, further comprising selecting an axial position of the IOL such that a distance between the anterior surface of the IOL and the iris of the eye having regular dimensions is between about 2.9 mm and about 3.5 mm.

8. A method of optimizing peripheral vision, comprising:
determining one or more physical and/or optical properties of a retina;
selecting an IOL based on the one or more physical properties of the retina, wherein the IOL is rotationally symmetric about an axis intersecting the retina at the fovea when implanted in an eye of a patient, the IOL having an anterior surface and a posterior surface, the IOL being configured to receive ambient light refracted from the cornea of the eye and focus at least a portion of on-axis incident light at a non-foveal region of the retina; and selecting an axial position of the IOL such that the anterior surface of the IOL is positioned between about 3.5 mm and 4.5 mm behind the iris of the eye having regular dimensions that optimizes optical quality at the non-foveal region of the retina to be less than or equal to a peripheral threshold MTF at the non-foveal region of the retina, the peripheral threshold MTF being dependent on one or more physical and/or optical properties of the retina.

9. The method of claim 8, wherein the optical properties of the retina include a geographical map of retinal functionality.

10. The method of claim 8, wherein the optical properties of the retina include the shape of the retina.

11. The method of claim 8, wherein determining one or more physical and/or optical properties of a retina includes measuring a shape of the retina of a patient or determining a size and location of a retinal scotoma in a patient.

12. The method of claim 8, further comprising implanting the selected IOL in the eye of the patient.

13. A multifocal IOL for optimizing peripheral vision comprising:

an optic comprised of at least two zones with each zone producing a focused image centered around a different part of the retina and wherein each zone has essentially the same dioptric power, the two zones including an inner zone and an outer zone, wherein the inner zone is spherical for focusing an image at the foveal region of retina and the outer zone comprises a spherical lens combined with a prism for focusing an image at a spot spaced away from the foveal region of the retina, the inner and the outer zone being connected by a transition zone having a step height value in a range between about 0.5 microns and about 4 microns, and wherein the optic is configured to reduce peripheral astigmatism.

14. The multifocal IOL of claim 13, wherein the add powers of the at least two zones are about zero diopters.

15. The multifocal IOL of claim 13, wherein no image is formed in a portion of the retina between the different parts of the retina.

* * * * *